United States Patent
Uehara et al.

(10) Patent No.: US 12,050,313 B2
(45) Date of Patent: Jul. 30, 2024

(54) OPERATION MEMBER FIXING MECHANISM AND ENDOSCOPE

(71) Applicant: OLYMPUS CORPORATION, Tokyo (JP)

(72) Inventors: Shohei Uehara, Fuchu-shi (JP); Reiji Koyama, Kawagoe-shi (JP); Yuta Nakai, Tachikawa-shi (JP)

(73) Assignee: OLYMPUS CORPORATION, Tokyo (JP)

( * ) Notice: Subject to any disclaimer, the term of this patent is extended or adjusted under 35 U.S.C. 154(b) by 657 days.

(21) Appl. No.: 17/215,965

(22) Filed: Mar. 29, 2021

(65) Prior Publication Data

US 2021/0212552 A1    Jul. 15, 2021

Related U.S. Application Data

(63) Continuation of application No. PCT/JP2018/036699, filed on Oct. 1, 2018.

(51) Int. Cl.
  *A61B 1/005*    (2006.01)
  *A61B 1/00*    (2006.01)
  *G02B 23/24*    (2006.01)

(52) U.S. Cl.
  CPC ...... *G02B 23/2476* (2013.01); *A61B 1/00042* (2022.02); *A61B 1/0052* (2013.01)

(58) Field of Classification Search
  CPC ............. A61B 1/00066; A61B 1/0052; A61M 25/0136
  USPC ................................... 74/531, 553; 600/148
  See application file for complete search history.

(56) References Cited

U.S. PATENT DOCUMENTS

| | | | | |
|---|---|---|---|---|
| 4,742,816 A | * | 5/1988 | Suzuki | A61B 1/0052 600/134 |
| 4,825,850 A | * | 5/1989 | Opie | A61B 1/0052 600/122 |
| 5,329,887 A | * | 7/1994 | Ailinger | A61B 1/0052 600/148 |

(Continued)

FOREIGN PATENT DOCUMENTS

| | | |
|---|---|---|
| EP | 2 692 277 A1 | 2/2014 |
| EP | 2 837 323 A1 | 2/2015 |

(Continued)

OTHER PUBLICATIONS

International Search Report dated Dec. 11, 2018 received in PCT/JP2018/036699.

*Primary Examiner* — Michael J Carey
*Assistant Examiner* — Stephen Floyd London
(74) *Attorney, Agent, or Firm* — Scully, Scott, Murphy & Presser, P.C.

(57) ABSTRACT

An operation member fixing mechanism includes: a plate member, an elastic member including a facing region, a protruding portion, a fixing lever, and a fixing knob. The protruding portion has a predetermined rigidity so as to allow the facing region to separate from the plate member when a compressed state is switched to a released state with a fixing lever and a fixing knob. The operation member fixing mechanism further includes a lubricant layer for reducing a sliding resistance of the protruding portion to the plate member in the released state and a cutout portion formed by cutting a contact surface of the facing region, the contact surface being a surface to be in contact with the plate member.

12 Claims, 6 Drawing Sheets

(56) References Cited

U.S. PATENT DOCUMENTS

| | | | | |
|---|---|---|---|---|
| 5,507,717 | A | * | 4/1996 | Kura .................. A61B 1/0052 600/146 |
| 2001/0037051 | A1 | * | 11/2001 | Fujii .................. A61B 1/0052 600/146 |
| 2007/0255103 | A1 | | 11/2007 | Maruyama |
| 2012/0277535 | A1 | * | 11/2012 | Hoshino ............ A61B 1/00066 600/146 |
| 2013/0158379 | A1 | * | 6/2013 | Selkee .................. A61B 5/283 604/95.04 |
| 2014/0058323 | A1 | | 2/2014 | Hoshino |
| 2014/0296640 | A1 | | 10/2014 | Hoshino |

FOREIGN PATENT DOCUMENTS

| | | |
|---|---|---|
| JP | 2003-061903 A | 3/2003 |
| JP | 2004-351221 A | 12/2004 |
| JP | 2007-289466 A | 11/2007 |
| JP | 2010220800 A | 10/2010 |
| JP | 2013-223735 A | 10/2013 |
| WO | 2013/061690 A1 | 5/2013 |
| WO | 2014/065093 A1 | 5/2014 |

* cited by examiner

OPERATION MEMBER FIXING MECHANISM AND ENDOSCOPE

CROSS-REFERENCE TO RELATED APPLICATION

This application is a continuation application of PCT/JP2018/036699 filed on Oct. 1, 2018, the entire contents of which are incorporated herein by this reference.

BACKGROUND OF THE INVENTION

1. Field of the Invention

The present invention relates to an operation member fixing mechanism and an endoscope that include a switching section configured to switch between a compressed state and a released state of an elastic member. In the compressed state, a sliding resistance is generated between the elastic member and a plate member, and in the released state, compression of the elastic member to the plate member is released to thereby reduce the sliding resistance.

2. Description of the Related Art

In recent years, endoscopes have been widely used in medical fields and industrial fields. Endoscopes for use in the medical fields are capable of observing an organ in a body cavity by inserting an elongated insertion portion into the body cavity as a subject, and performing various kinds of treatment by using, as needed, a treatment instrument inserted into a treatment instrument insertion channel provided in the endoscopes.

Endoscopes for use in the industrial fields are capable of performing inspection such as observation and various kinds of treatment of flaws, corrosion, and the like of a site to be inspected in an object such as a jet engine, a pipe of a factory, etc., by inserting an elongated insertion portion of the endoscopes into the object.

A configuration of an endoscope is known, in which a bending portion bendable in a plurality of directions is provided in an insertion portion of the endoscope.

The bending portion improves the advancing performance of the insertion portion at a flex portion in a tubular path, and also varies an observation direction of an observation optical system provided in the distal end portion located on the distal end side with respect to the bending portion in the insertion portion.

The bending portion is configured to bend in either a left direction or a right direction by rotation operation of a bending knob for left-right bending provided on an operation portion. Furthermore, the bending portion is configured to bend in either an up direction or a down direction by rotation operation of a bending knob for up-down bending provided on the operation portion.

In addition, a bending operation knob fixing mechanism is also known, in which a lock lever for up-down bending fixing and a lock knob for left-right bending fixing are provided on the operation portion.

The lock lever for up-down bending fixing is configured to fix a bending angle of the bending portion bent in the up direction or the down direction by the rotation operation of the bending knob for up-down bending, that is, a rotation position of the bending knob for up-down bending. In addition, the lock knob for left-right bending fixing is configured to fix a bending angle of the bending portion bent in the left direction or the right direction by the rotation operation of the bending knob for right-left bending, that is, a rotation position of the bending knob for left-right bending.

The bending operation knob fixing mechanism is provided for each of the bending knob for up-down bending and the bending knob for left-right bending.

The bending operation knob fixing mechanism is configured to fix the rotation of the bending knob by generating a sliding resistance between an annular-shaped elastic member and two annular-shaped plate members. For example, the sliding resistance is generated by bringing the annular-shaped elastic member configured to rotate together with the bending knob into a compressed state by a switching section in accordance with rotation of a fixing lock lever or a fixing lock knob in one direction. The compressed state is achieved by the annular-shaped elastic member being sandwiched between the two annular-shaped plate members to be adhered closely to and compressed by the plate members.

In addition, Japanese Patent Application Laid-Open Publication No. 2004-351221 discloses a configuration of a bending operation knob fixing mechanism in which a protruding portion is provided on a contact surface of an elastic member which is in contact with a plate member. The protruding portion protrudes with respect to the contact surface and constantly contacts the plate member.

The protruding portion is configured to allow the contact surface of the elastic member, which is adhered closely to the plate member, to easily release from the plate member by a reaction force (rigidity) of the protruding portion in the operation for separating the plate member from the elastic member by the switching section in accordance with the rotation of the fixing lock lever or the fixing lock knob in the direction opposite to the above-described one direction, at the time of releasing the rotation fixed state of the bending knob, in other words, at the time of bringing the elastic member into a released state where the above-described compressed state of the elastic member is released.

Note that the protruding portion is crushed by the plate member when the rotation of the bending knob is fixed. Accordingly, the contact surface of the elastic member comes into contact with and adhered closely to the plate member, regardless of the presence of the protruding portion.

As described above, the protruding portion constantly contacts the plate member. Therefore, the rigidity of the protruding portion is set to be low in order to prevent the contact of the protruding portion with the plate member from becoming a resistance to the rotation of the elastic member in the rotation non-fixed state of the bending knob.

Furthermore, a configuration is also known, in which grease or the like, which serves as a lubricant layer for reducing the sliding resistance of the protruding portion to the plate member, is applied between the elastic member and the plate member.

SUMMARY OF THE INVENTION

An operation member fixing mechanism according to one aspect of the present invention includes: a plate member provided in an operation member of an endoscope; an elastic member disposed so as to face the plate member in the operation member, the elastic member being elastically deformable and including a facing region that faces the plate member; at least one protruding part provided to the elastic member in the operation member, the protruding part protruding further to the plate member than the facing region, the protruding part being elastically deformable; and a switching member configured to be capable of switching between a compressed state and a released state, the compressed state being a state where the elastic member and the protruding part are compressed to the plate member, to thereby generate a sliding resistance between the plate member and the elastic member and the protruding part, the released state being a state where compression of the elastic member and the protruding part to the plate member is released, to thereby reduce the sliding resistance. The switching member causes the protruding part and the facing region to adhere closely to the plate member in the compressed state, and causes the facing region to separate from the plate member, with the protruding part kept in contact with the plate member in the released state, and the protruding part has a predetermined rigidity for allowing the facing region to separate from the plate member, when the compressed state is switched to the released state by the switching member. The operation member fixing mechanism further includes: a lubricant layer disposed between the plate member and the elastic member and protruding part, the lubricant layer reducing the sliding resistance of the protruding part to the plate member in the released state; and at least one cutout formed by cutting out a part of a contact surface of the facing region of the elastic member, the contact surface being a surface to be in contact with the plate member.

An endoscope according to one aspect of the present invention includes an operation member fixing mechanism that includes: a plate member provided in an operation member; an elastic member disposed so as to face the plate member in the operation member, the elastic member being elastically deformable and including a facing region that faces the plate member; at least one protruding part provided to the elastic member in the operation member, the protruding part protruding further to the plate member than the facing region, the protruding part being elastically deformable; and a switching member configured to be capable of switching between a compressed state and a released state, the compressed state being a state where the elastic member and the protruding part are compressed to the plate member, to thereby generate a sliding resistance between the plate member and the elastic member and protruding part, the released state being a state where compression of the elastic member and the protruding part to the plate member is released, to thereby reduce the sliding resistance. The switching member causes the protruding part and the facing region to adhere closely to the plate member in the compressed state, and causes the facing region to separate from the plate member, with the protruding part kept in contact with the plate member in the released state, and the protruding part has a predetermined rigidity for allowing the facing region to separate from the plate member, when the compressed state is switched to the released state by the switching member. The operation member fixing mechanism further includes: a lubricant layer disposed between the plate member and the elastic member and protruding part, the lubricant layer reducing the sliding resistance of the protruding part to the plate member in the released state; and at least one cutout formed by cutting out a part of a contact surface of the facing region of the elastic member, the contact surface being a surface to be in contact with the plate member.

DETAILED DESCRIPTION OF THE PREFERRED EMBODIMENT(S)

Hereinafter, an embodiment of the present invention will be described with reference to drawings.

Figure 1:
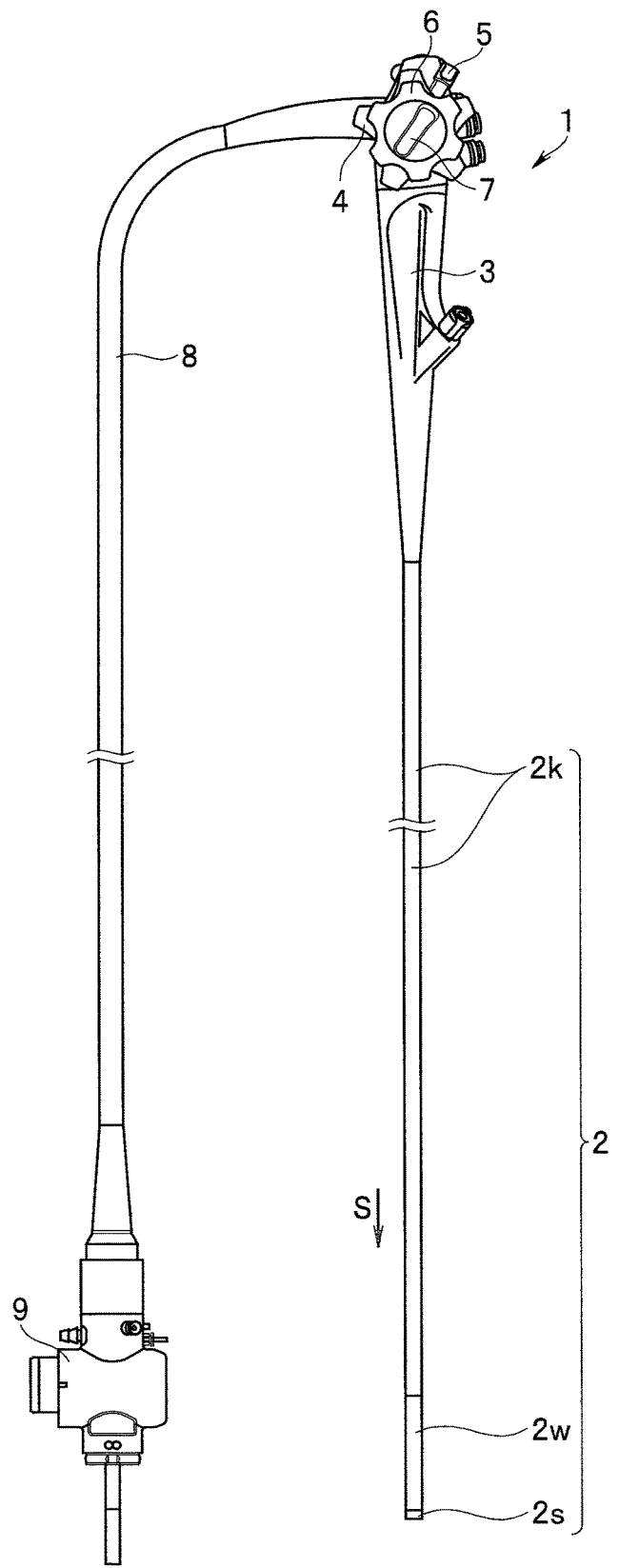
FIG. 1 illustrates an appearance of an endoscope including, on an operation portion, a bending operation knob fixing mechanism according to a present embodiment.

FIG. 1 illustrates an appearance of an endoscope including, on an operation portion, a bending operation knob fixing mechanism according to the present embodiment.

As illustrated in FIG. 1, an endoscope 1 includes a main part configured by: an insertion portion 2 configured to be inserted into a subject (or an object); an operation portion 3 provided continuously with a proximal end side of an insertion direction S of the insertion portion 2; a universal cord 8 extended from the operation portion 3; and a connector 9 provided at an extension end of the universal cord 8.

Note that the endoscope 1 is electrically connected to external apparatuses such as a control apparatus, illumination apparatus, etc., through the connector 9.

The operation portion 3 includes an up-down bending operation knob (hereinafter, just referred to as bending knob) 4 and a left-right bending operation knob (hereinafter, just referred to as bending knob) 6. The bending knob 4 is configured to cause a bending portion 2w, to be described later, of the insertion portion 2 to bend in up and down directions. The bending knob 6 is configured to cause the bending portion 2w to bend in left and right directions.

The operation portion 3 further includes a fixing lever 5 and a fixing knob 7. The fixing lever 5 is a switching section configured to fix the rotation position of the bending knob 4. The fixing knob 7 is a switching section configured to fix the rotation position of the bending knob 6.

A bending operation knob fixing mechanism 100 (see FIG. 2) to be described later is provided for the bending knob 4 and the fixing lever 5, and provided also for the bending knob 6 and fixing knob 7.

The insertion portion 2 includes a distal end portion 2s, the bending portion 2w, and a flexible tube portion 2k, and is formed in an elongated shape along an insertion direction S.

The distal end portion 2s includes inside thereof an image pickup unit, not illustrated, for observing an inside of a subject, an illumination unit for illuminating the inside of the subject, and the like.

The bending portion 2w is configured to bent in four directions, for example, up, down, left, and right directions by the rotation operation of the bending knobs 4 and 6, to thereby vary an observation direction of the image pickup unit provided in the distal end portion 2s and improve the insertion performance of the distal end portion 2s in the subject. Furthermore, the flexible tube portion 2k is provided continuously with the proximal end side of the bending portion 2w.

Next, description will be made on the configuration of the bending operation knob fixing mechanism provided on the operation portion 3, with reference to FIGS. 2 to 6.

Figure 2:
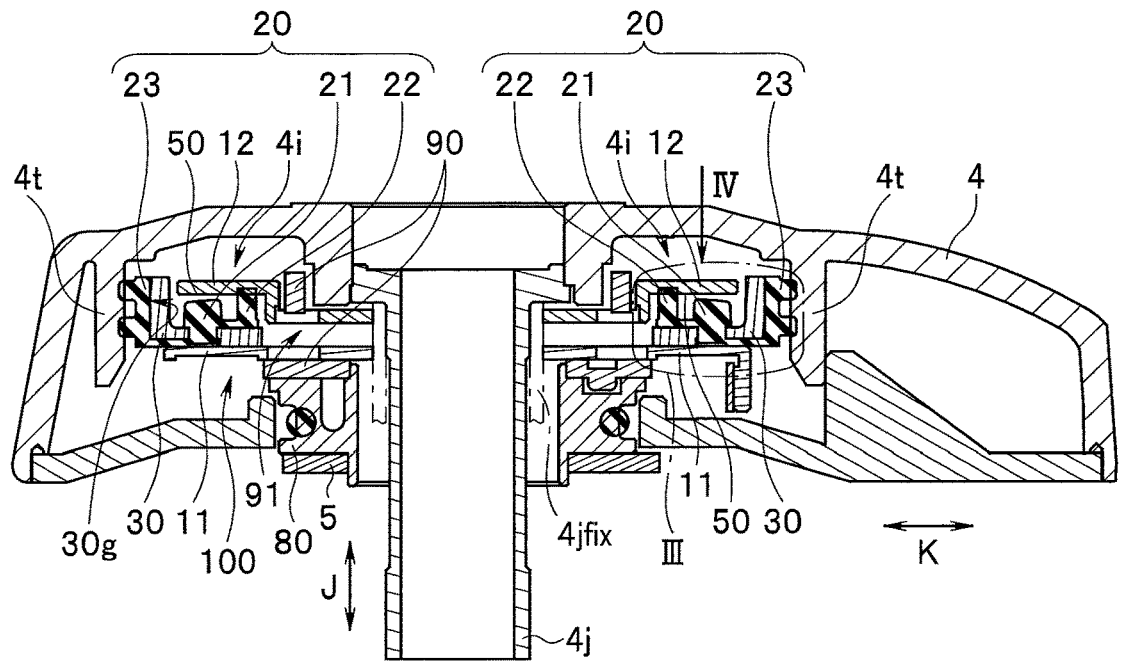
FIG. 2 is a cross-sectional view illustrating an outline of a configuration of the bending operation knob fixing mechanism, which is provided in an up-down bending operation knob, in FIG. 1.
Figure 3:
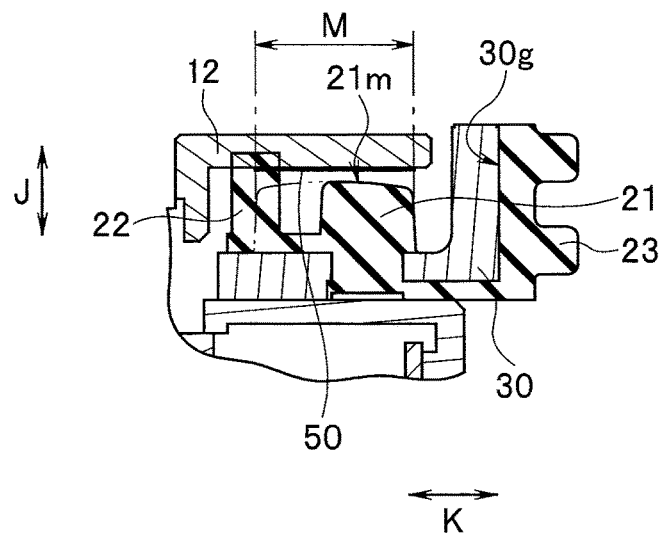
FIG. 3 is a partial cross-sectional view of the configuration of the bending operation knob fixing mechanism in FIG. 2, which illustrates a part enclosed by the line III in FIG. 2 in an enlarged manner.

FIG. 2 is a cross-sectional view illustrating an outline of a configuration of the bending operation knob fixing mechanism, which is provided in an up-down bending operation knob, in FIG. 1. FIG. 3 is a partial cross-sectional view of the configuration of the bending operation knob fixing mechanism in FIG. 2, which illustrates a part enclosed by the line III in FIG. 2 in an enlarged manner.

Figure 4:
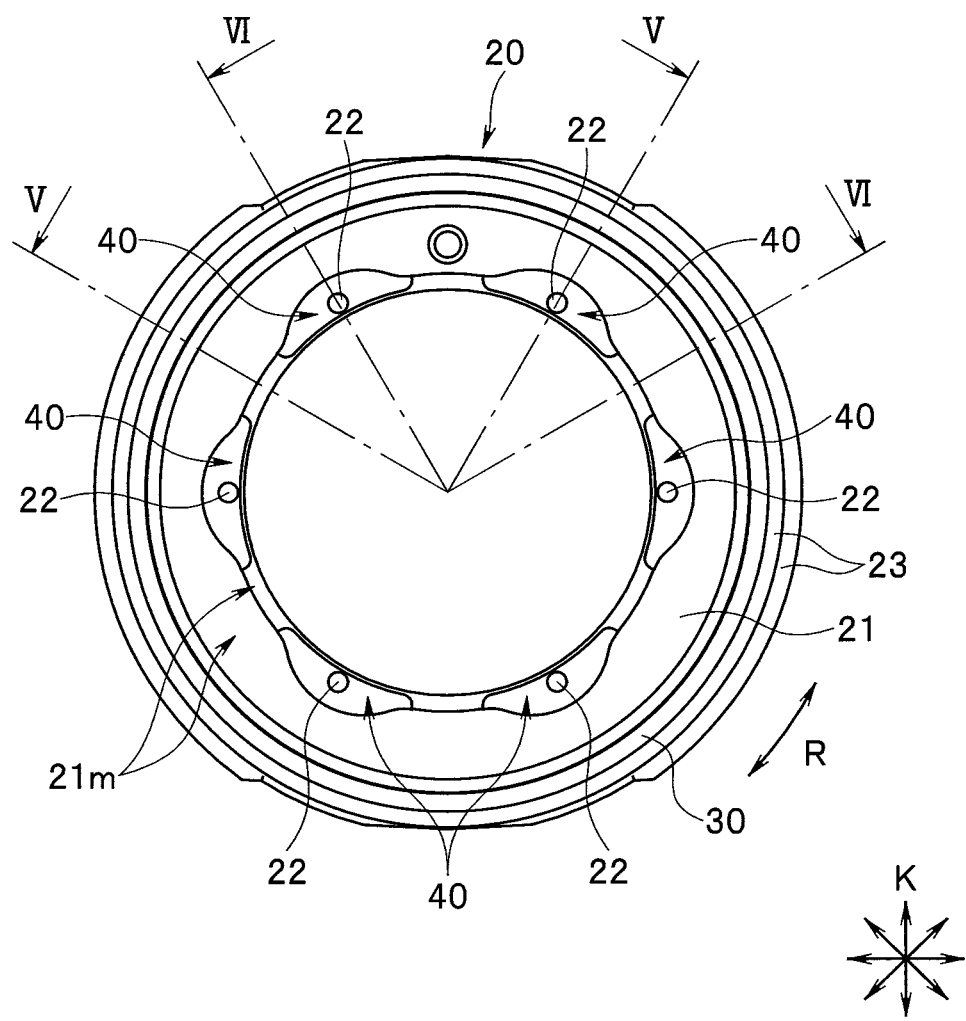
FIG. 4 is a plan view of an elastic member in the bending operation knob fixing mechanism in FIG. 2, when viewed from the IV direction in FIG. 2.
Figure 5:
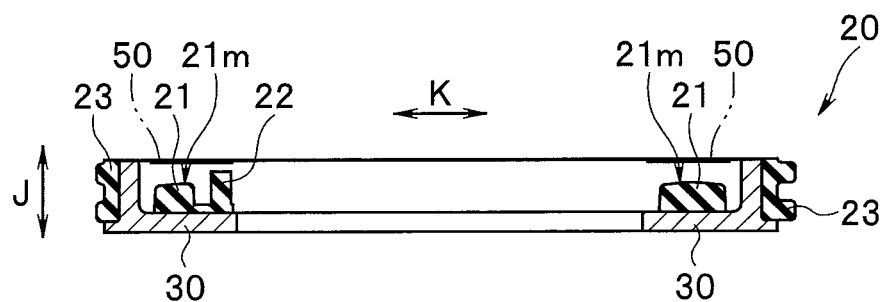
FIG. 5 is a cross-sectional view of the elastic member taken along the line V-V in FIG. 4.
Figure 6:
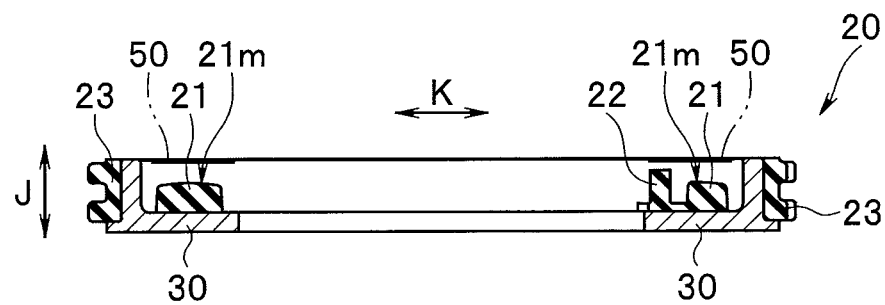
FIG. 6 is a cross-sectional view of the elastic member taken along the line VI-VI in FIG. 4.

FIG. 4 is a plan view of an elastic member in the bending operation knob fixing mechanism in FIG. 2, when viewed from the IV direction in FIG. 2. FIG. 5 is a cross-sectional view of the elastic member taken along the line V-V in FIG. 4. FIG. 6 is a cross-sectional view of the elastic member taken along the line VI-VI in FIG. 4. The configuration of the bending operation knob fixing mechanism 100 will be described below by taking the configuration related to the bending knob 4 and the fixing lever 5, as an example.

As illustrated in FIG. 2, the bending operation knob fixing mechanism 100 includes a main part configured by a first plate member 11, a second plate member 12, an elastic member 20, the fixing lever 5, and a lubricant layer 50.

Both of the first plate member 11 and the second plate member 12 are provided in an inner portion 4i of the bending knob 4.

In addition, both of the first plate member 11 and the second plate member 12 are formed in an annular shape, and fitted to an outer circumference of a fixing shaft 4jfix so as not to rotate in a circumferential direction R.

Specifically, the outer circumference of the fixing shaft 4jfix is formed in a shape of a partially cut circle, for example, a D-shape, at the position to which the first plate member 11 and the second plate member 12 are fitted. In addition, each of holes of the first plate member 11 and the second plate member 12 fitted to the fixing shaft 4jfix is formed in a shape in which corner portions are formed at a part of the circumference. With such a configuration, the corner portions of the holes of the first plate member 11 and the second plate member 12 are caught by the partially cut part of the fixing shaft 4jfix, to thereby prevent the first plate member 11 and the second plate member 12 from rotating with respect to the fixing shaft 4jfix.

Therefore, the first plate member 11 and the second plate member 12 do not rotate together with the rotation shaft 4j, that is, the bending knob 4.

In the inner portion 4i of the bending knob 4, the second plate member 12 and the elastic member 20 are disposed so as to face each other in a facing direction J. The second plate member 12 is disposed separately from the first plate member 11 so as to be stacked over the first plate member 11 along the facing direction J. The facing direction J substantially coincides (substantially parallel to) an axis direction of the rotation shaft 4i and is substantially parallel to a protruding axis of a protruding portion 22 to be described later. Note that the elastic member 20 is disposed so as to be sandwiched between the first plate member 11 and the second plate member 12.

Furthermore, the second plate member 12 is configured to be movable along the facing direction J in accordance with the rotation operation of the fixing lever 5.

The fixing lever 5 is fixed to a pivot block 80 which is a part of the switching section provided in an inner portion 6i of the bending knob 6. When the rotation operation of the fixing lever 5 is performed, the pivot block 80 and a cam ring 90, which are fixed integrally with the fixing lever 5, rotate.

The cam ring 90 has a groove 91 whose width JH in the facing direction J changes in the circumferential direction R, and the first plate member 11 and the second plate member 12 are held by the groove 91. Even when the cam ring 90 is rotated, the first plate member 11 and the second plate member 12 do not rotate, since the rotation direction of the first and second plate members is fixed by the fixing shaft 4jfix.

Figure 7:
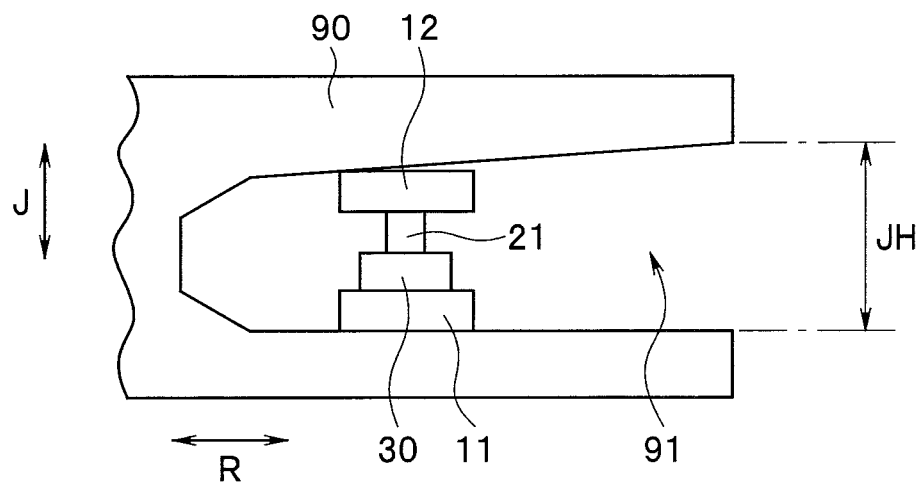
FIG. 7 is a partial development view in a circumferential direction of a cam ring in FIG. 2.

As illustrated in FIG. 7, the spacing in the facing direction J between the first plate member 11 and the second plate member 12 that are held by the groove 91 of the cam ring 90 changes by the second plate member 12 moving upward or downward in the facing direction J in FIG. 2 with the change in the groove width JH in accordance with the rotation of cam ring 90. With such a configuration, the fixing lever 5 causes the cam ring 90 to rotate, to thereby change the positions of the first plate member 11 and the second plate member 12. As a result, the fixing lever 5 switches the elastic member 20 between the compressed state and the released state.

Figure 8:
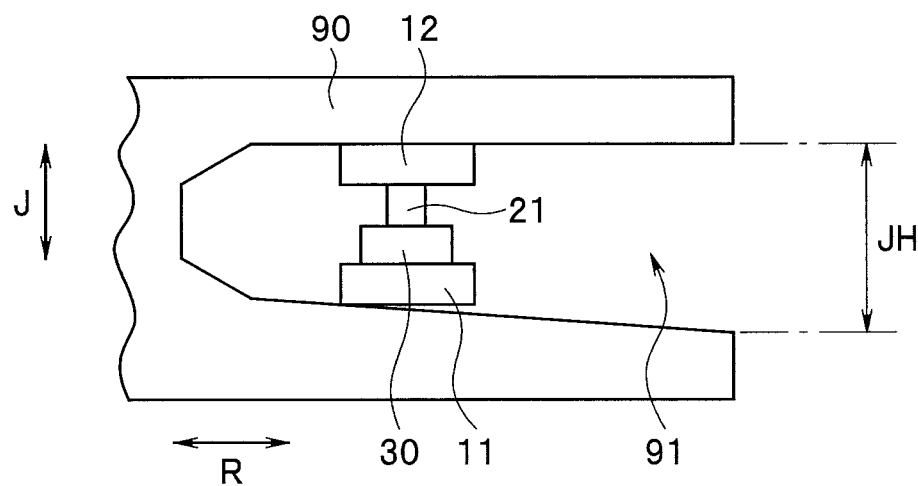
FIG. 8 is a partial development view of the cam ring, which illustrates a modification of a groove formed in the cam ring in FIG. 7.

Note that the fixing lever 5 may switch the elastic member 20 between the compressed state and the released state by moving the first plate member 11 upward or downward in the facing direction J in FIG. 2 by using an inclined surface of the groove 91 in FIG. 8. The inclined surface is formed on the opposite side in the facing direction J of the inclined surface of the groove 91 illustrated in FIG. 7.

Figure 9:
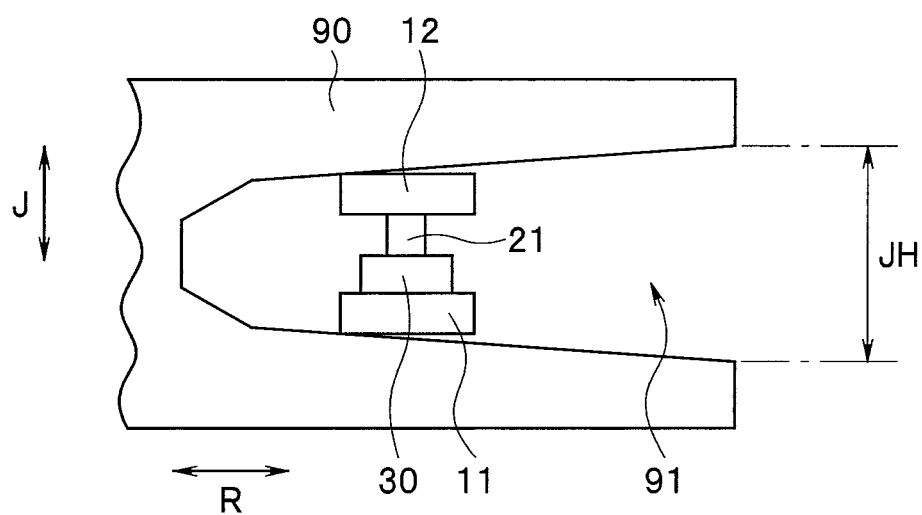
FIG. 9 is a partial development view of the cam ring, which illustrates another modification of the groove formed in the cam ring in FIG. 7.

In addition, the fixing lever 5 may switch the elastic member 20 between the compressed state and the released state by moving both of the first plate member 11 and the second plate member 12 upward or downward in the facing direction J in FIG. 2 in accordance with the shape of the groove 91 as illustrated in FIG. 9.

Note that the compressed state indicates a state where a sliding resistance is generated between the elastic member 20 and the second plate member 12 by compressing the elastic member 20 between the first plate member 11 and the second plate member 12 in the facing direction J.

The released state indicates a state where the compressed state of the elastic member 20 by the first plate member 11 and the second plate member 12 is released, to thereby reduce the sliding resistance.

As described later, the compressed state indicates the rotation fixed state of the bending knob 4 and the released state indicates the rotation non-fixed state of the bending knob 4.

In addition, a wide variety of known configurations are applicable to the configuration for moving the second plate member 12 along the facing direction J by using the fixing lever 5.

The elastic member 20 is formed in an annular shape as illustrated in FIG. 4, so as to be loosely fitted on the outer circumference of the rotation shaft 4j.

Furthermore, the elastic member 20 is disposed in the inner portion 4i of the bending knob 4 between the first plate member 11 and the second plate member 12 in the facing direction J so as to face both of the plate members 11 and 12, and configured to be elastically deformable.

The elastic member 20 is in contact with the first plate member 11 through a fixing member 30. Therefore, when the bending knob 4 is rotated, the elastic member 20 is rotatable while sliding in contact with the first plate member 11.

As illustrated in FIG. 2, the elastic member 20 includes a main part configured by a facing region 21, protruding portions 22 that protrude in an axis direction parallel to the facing direction J, and a bending knob contacting portion 23.

In the compressed state, the above-described switching section causes the facing region 21 to adhere closely to the second plate member 12, while causing the protruding portion 22 to adhere closely to the second plate member 12. On the other hand, in the released state, the switching section causes the facing region 21 to separate from the second plate member 12 along the facing direction J, with the protruding portion 22 kept in contact with the second plate member 12.

Specifically, as illustrated in FIGS. 2 to 6, the facing region 21 is separated from the second plate member 12 in the above-described released state. On the other hand, in the above-described compressed state, the facing region 21 is brought into a state where a contact surface 21$m$ is adhered closely to the second plate member 12 circumferentially (in a circular manner) in a contact range M.

In addition, the contact surface 21$m$ is formed such that the cross section thereof has a projected curved surface shape, as illustrated in FIG. 2, FIG. 3, FIG. 5, and FIG. 6. Due to such a shape, immediately after the contact surface 21$m$ contacts the second plate member 12, the contact surface 21$m$ comes into line contact with the second plate member 12 circumferentially (in a circular manner).

The contact surface 21$m$ may have a triangular cross section instead of the curved surface shape so as to come into line contact with the second plate member 12 circumferentially (in a circular manner). In other words, the contact surface 21$m$ may have any shape as long as the contact surface 21$m$ can come into line contact with the second plate member 12.

In addition, as illustrated in FIG. 4, on the contact surface 21$m$ of the facing region 21, cutout portions 40 are formed by cutting out a part of the contact surface 21$m$.

As illustrated in FIG. 4, each of the cutout portions 40 has a shape cut out in a predetermined range so as to be recessed with respect to the elastic member 20 in a radius direction K of the elastic member 20. In addition, each of the cutout portions 40 has a shape recessed from the contact surface 21$m$ along the facing direction J.

As illustrated in FIG. 4, the cutout portions 40 are disposed near a plurality of protruding portions 22 in the circumferential direction R of the elastic member 20. Specifically, a plurality of cutout portions 40 are disposed respectively at positions corresponding to the plurality of protruding portions 22 in the circumferential direction R.

Note that only one cutout portion 40 may be formed on the contact surface 21$m$ in the circumferential direction R.

In addition, the cutout portions 40 may be disposed at positions separated from the protruding portions 22. However, if the cutout portions 40 are disposed near the protruding portions 22, it is not necessary to ensure additional regions for forming the cutout portions 40, which results in a reduction in the diameter of the contact surface 21$m$. Thus, size reduction of the elastic member 20, that is, size reduction of the bending operation knob fixing mechanism 100 can be achieved.

In addition, the cutout portions 40 communicate with an outside of the second plate member 12 or the elastic member 20, that is, the inner portion 4$i$ of the bending knob 4 in the above-described compressed state, that is, the state where the elastic member 20 is adhered closely to the second plate member 12.

Each of the protruding portions 22 is elastically deformable. As illustrated in FIGS. 2 to 6, each of the protruding portions 22 protrudes in a columnar shape along the facing direction J further to the second plate member 12 than the facing region 21 in the bending knob 4. The protruding portions 22 are formed so as to constantly contact the second plate member 12 in both of the above-described compressed state and released state. In the present embodiment, description has been made by taking the case where the protruding portions 22 are formed integrally with the elastic member 20 as an example. However, the protruding portions 22 may be formed separately from the elastic member 20. In other words, the protruding portions 22 do not have to constitute the elastic member 20, but may be connected to the elastic member 20.

In the above-described compressed state, the protruding portions 22 are crushed along the facing direction J by the second plate member 12 such that the contact surface 21$m$ of the facing region 21 comes into contact with the second plate member 12.

In addition, the protruding portions 22 have a predetermined rigidity for allowing the facing region 21 to separate from the second plate member 12 along the facing direction J by the reaction force with which the protruding portions 22 return from the crushed state to the original state when the above-described compressed state is switched to the released state by the fixing lever 5.

Note that the predetermined rigidity indicates a rigidity of a degree that does not cause a large resistance to the rotation of the elastic member 20 and does not cause an increase in the rotation operation force amount of the bending knob 4 regardless of the contact of the protruding portions 22 with the second plate member 12 in the above-described released state.

Furthermore, the plurality of protruding portions 22 are provided in the circumferential direction R of the elastic member 20, as illustrated in FIG. 4.

As illustrated in FIGS. 2 and 3, the bending knob contact portion 23 is fixed to an outer circumferential surface 30$g$ of the fixing member 30 and is constantly in contact with a fixing wall 4$t$ that constitutes an inner circumferential surface located in the inner portion 4$i$ of the bending knob 4.

In the released state, on the one hand, when the bending knob 4 is rotated, the elastic member 20 rotates together with the bending knob 4, with the bending knob contact portion 23 abutting the fixing wall 4$t$. In other words, in the released state, the bending knob 4 is in the rotation non-fixed state.

In the compressed state, on the other hand, the elastic member 20 is sandwiched between the first plate member 11 and the second plate member 12, to thereby generate a sliding resistance (rotation resistance), and the sliding resistance is applied from the bending knob contact portion 23 to the fixing wall 4$t$.

Thus, a resistance is applied to the rotation of the bending knob 4. In other words, the bending knob contact portion 23 and the fixing member 30, which are contact members, transmit the sliding resistance generated in the compressed state to the fixing wall 4$t$.

Accordingly, in the compressed state, the bending knob 4 is in the rotation fixed state in which the rotation position of the bending knob 4 is fixed.

A lubricant, not illustrated, is applied between the fixing wall 4t and the bending knob contact portion 23. The bending knob contact portion 23 may be formed integrally with or separately from the facing region 21 and the protruding portions 22.

The lubricant layer 50 is made from grease, for example, and disposed (applied) between the second plate member 12 and the elastic member 20 in the facing direction J.

The lubricant layer 50 reduces the sliding resistance of the protruding portions 22 to the second plate member 12 in the released state.

Since other configurations of the bending operation knob fixing mechanism 100 is known, description thereof will be omitted.

Thus, in the present embodiment, the cutout portions 40 formed by cutting out a part of the contact surface 21m are formed on the contact surface 21m of the facing region 21 of the elastic member 20.

With such a configuration, even if the contract surface 21m of the facing region 21 is adhered closely to the second plate member 12 in the compressed state, the contact surface 21m is adhered closely to the second plate member 12 only in the contact range M as described above, and the parts of the facing region 21, in which the cutout portions 40 are formed, are not in contact with the second plate member 12.

Therefore, even if the protruding portions 22 do not have a high rigidity, due to an air layer created between the facing region 21 and the second plate member 12 by the cutout portions 40, the contact surface 21m can be easily separated from the second plate member 12 only with the reaction force of the protruding portions 22 in the released state.

In addition, in the above-described present embodiment, the contact surface 21m of the facing region 21 is formed in the curved surface shape. Therefore, in the state where the contact surface 21m just contacts the second plate member 12, the contact area of the contact surface 21m with the second plate member 12 is smaller than that in the case where the contact surface 21m is formed in a planar shape.

With such a configuration, a gap is likely to be created between the contact surface 21m and the second plate member 12 in the released state, the contact surface 21m easily separates from the second plate member 12 only with the reaction force of the protruding portions 22.

Thus, even if the protruding portions 22 do not have a high rigidity, the facing region 21 can be easily separated from the second plate member 12 when the elastic member 20 is switched from the compressed state to the released state.

In addition, the sliding resistance of the protruding portions 22 to the second plate member 12 can be reduced. In other words, the rotation operation force amount of the bending knob 4 in the released state can be reduced.

Thus, the present invention is capable of providing the bending operation knob fixing mechanism 100 having the configuration in which the close adhesion of the elastic member 20 to the second plate member 12 can be surely released and the rotation operation force amount of the bending knob 4 can be reduced when the rotation fixed state of the bending knob 4 is released.

In the above-described present embodiment, the bending operation knob fixing mechanism 100 is described by taking the configuration related to the bending knob 4 and the fixing lever 5 as an example. However, the configuration is not limited to the example, but the same is true on the bending operation knob fixing mechanism including the bending knob 6 and the fixing knob 7.

What is claimed is:

1. An operation member fixing mechanism for use in an endoscope, the operation member fixing mechanism comprising:
   a plate member configured to be provided in an operation member of the endoscope;
   an elastic member disposed in the operation member, the elastic member facing the plate member and being elastically deformable, the elastic member including a facing region that faces the plate member;
   at least one protruding part provided to the elastic member in the operation member, the at least one protruding part disposed in the operation member, the at least one protruding part facing the plate member and protruding further to the plate member than the facing region, the at least one protruding part being elastically deformable; and
   one of a lever or knob configured to switch each of the elastic member and the at least one protruding part between a compressed state and a released state, the compressed state being a state where each of the elastic member and the at least one protruding part are compressed to the plate member, to increase a sliding resistance between the plate member and each of the elastic member and the at least one protruding part, the released state being a state where compression of each of the elastic member and the at least one protruding part to the plate member is reduced relative to the compression state, to reduce the sliding resistance,
   wherein in the compressed state, the at least one protruding part and the facing region are each compressed to the plate member, and in the released state, the facing region is separated from the plate member and the at least one protruding part is kept in contact with the plate member.

2. The operation member fixing mechanism according to claim 1, wherein the at least one protruding part has a columnar shape and is disposed in at least one cutout.

3. The operation member fixing mechanism according to claim 2, wherein the plate member and the elastic member are formed in an annular shape, and the at least one protruding part comprises a plurality of protruding parts formed in a circumferential direction of the elastic member, and the at least one cutout comprises a plurality of cutouts disposed at positions corresponding to the plurality of protruding parts in the circumferential direction.

4. The operation member fixing mechanism according to claim 1, wherein at least one cutout communicates with one of an outside of the plate member or an outside of the elastic member in the compressed state.

5. The operation member fixing mechanism according to claim 1, wherein a contact surface of the facing region has a curved surface shape.

6. The operation member fixing mechanism according to claim 1, wherein
   the plate member comprises a first plate member;
   the operation member fixing mechanism further comprises and a second plate member stacked over the first plate member such that the elastic member is sandwiched between the first plate member and the second plate member, and
   one of the lever or knob switches between the compressed state and the released state by moving at least one of the first plate member or the second plate member in a stacking direction in which the first plate member and the second plate member are stacked.

7. The operation member fixing mechanism according to claim 6, further comprising a contact member disposed between an inner circumferential surface of the operation member and the elastic member, the contact member being configured to increase a sliding resistance between the inner circumferential surface of the operation member and the contact member in the compressed state.

8. The operation member fixing mechanism according to claim 6, wherein
one of the lever or knob includes a cam ring configured to rotate with respect to a rotation shaft of the operation member in accordance with an operation by an operator, the cam ring including a groove formed in a rotation direction, and
the first plate member and the second plate member are disposed in the groove, and a width of the groove in the stacking direction changes in the rotation direction.

9. An endoscope comprising the bending operation knob fixing mechanism according to claim 1.

10. The operation member fixing mechanism according to claim 1, wherein, in the released state, the at least one protruding part has a predetermined rigidity for biasing the plate member away from the facing region to separate the facing region from the plate member.

11. The operation member fixing mechanism according to claim 10, wherein the operation member fixing mechanism further comprises a lubricant layer disposed between the plate member and the at least one protruding part, the lubricant layer reducing the sliding resistance of the at least one protruding part to the plate member in the released state relative to the sliding resistance of the at least one protruding part to the plate member in the released state without the lubricant.

12. The operation member fixing mechanism according to claim 11, wherein the elastic member having at least one cutout in a contact surface of the facing region, the contact surface being a surface in contact with the plate member in the compressed state.

* * * * *